(12) United States Patent
Morita

(10) Patent No.: US 7,638,024 B2
(45) Date of Patent: Dec. 29, 2009

(54) CAPILLARY ELECTROPHORESIS METHOD

(75) Inventor: Naoki Morita, Kyoto (JP)

(73) Assignee: Shimadzu Corporation, Kyoto-Fu (JP)

( * ) Notice: Subject to any disclaimer, the term of this patent is extended or adjusted under 35 U.S.C. 154(b) by 526 days.

(21) Appl. No.: 11/486,142

(22) Filed: Jul. 14, 2006

(65) Prior Publication Data
US 2007/0012568 A1     Jan. 18, 2007

(30) Foreign Application Priority Data
Jul. 14, 2005     (JP)     ............... 2005-205075

(51) Int. Cl.
  *G01N 27/447*     (2006.01)
(52) U.S. Cl. ...................... 204/452; 204/451
(58) Field of Classification Search ......... 204/601–605, 204/451–455
See application file for complete search history.

(56) References Cited
U.S. PATENT DOCUMENTS

| | | | |
|---|---|---|---|
| 5,139,630 A * | 8/1992 | Chen ........................... | 204/451 |
| 5,228,960 A * | 7/1993 | Liu et al. ..................... | 204/451 |
| 2002/0033336 A1 | 3/2002 | Liu et al. | |
| 2005/0027111 A1 | 2/2005 | Chow et al. | |

FOREIGN PATENT DOCUMENTS

| | | | |
|---|---|---|---|
| EP | 1 178 305 A2 | 2/2002 | |
| EP | 1178305 A2 * | 2/2002 | |
| EP | 1 600 771 A1 | 11/2005 | |
| WO | WO 02/090965 A1 | 11/2002 | |

OTHER PUBLICATIONS

Joshua Edel ("Thin-film polymer light emitting diodes as integrated excited sources for microscale capillary electrophoresis," Lab Chip, 2004, 4, 136-140).*
Xing-Zhang Wu ("Whole-column fluorescence-imaged capillary electrophoresis," Electrophoresis 2004, 25, 3820-3824).*
5-carboxyfluorescein Biotium catalog entry downloaded from www.biotium.com on Mar. 15, 2009.*
Hitachi Chemical Technical Report No. 40(Jan. 2003).

* cited by examiner

*Primary Examiner*—Alex Noguerola
(74) *Attorney, Agent, or Firm*—Sughrue Mion, PLLC

(57) ABSTRACT

Disclosed is a capillary electrophoresis method for simultaneously electrophoresing an unknown sample and an internal standard material, determining an earliest peak as a peak derived from the internal standard material, and identifying the unknown sample on the basis of the internal standard substance-derived peak. The internal standard substance consists of a fluorescent substance or a salt thereof which has a positive or negative net charge of 2 or more in an electrolyte solution used for capillary electrophoresis. An earliest one of detected peaks is determined as a peak derived from the internal standard substance, and the remaining peaks are identified on the basis of the internal standard substance-derived peak.

4 Claims, 2 Drawing Sheets

CAPILLARY ELECTROPHORESIS METHOD

BACKGROUND OF THE INVENTION

1. Field of the Invention

The present invention relates to a capillary electrophoresis method using an internal standard substance.

2. Description of the Related Art

Capillary electrophoresis is a technique in which a certain voltage is applied across opposite ends of a capillary having an inner diameter of about 100 µm to electrophorese substances in the capillary filled with an electrolytic solution, and the electrophoresed substances are detected using a detector to measure a migration time of each peak from a signal of the detector and identify the peak based on the migration time. In reality, even if electrophoresis conditions, such as applied voltage and temperature, are kept constant, a migration time of each substance generally varies in every migration. These variations cause difficulty in accurately identifying the substance based on only the migration time thereof.

As one solution to this problem, there has been known a technique in which an internal standard substance is added to a sample solution and electrophoresed together with sample components, and a migration time of each peak of the sample components is corrected using a migration time of the internal standard substance as an index, before identification. For example, when a sample component is a DNA or RNA, and it is intended to estimate a size thereof, at least two types of internal standard substances capable of being separated with a certain predetermined resolution and detected in both sides of a molecular weight range (on the side of a low molecular weight and on the side of a high molecular weight: hereinafter referred to respectively as "low-molecular-weight-side (LMW-side) internal standard substance" and "high-molecular-weight-side (HMW-side) internal standard substance") are added to a sample solution, and a migration time of each peak of the sample components is corrected using respective detection times of the LMW-side and HMW-side internal standard substances as indexes, on a program basis, before estimating a size of an RNA or DNA. In the following Non-Patent Publication 1, a 50-bp double-stranded DNA is used as a LMW-side internal standard substance, and an 800-bp double-stranded DNA is used as a HMW-side internal standard substance.

[Non-Patent Publication 1] Hitachi Chemical Technical Report No. 40 (2003-1)

SUMMARY OF THE INVENTION

A conventional LMW-side internal standard substance is likely to be detected later than an oligo-DNA (about 7 to 20-mer) contained in a sample solution. Such an oligo-DNA is essentially used as a primer in a polymerase chain reaction (PCR) widely utilized in preparation of a DNA sample, and therefore generally contained in a sample solution. Further, in most data analyses of an electrophoretic result, an earliest one of detected peaks is recognized as a peak derived from a LMW-side internal standard substance, and respective migration times of the remaining detected peaks are corrected based on the earliest peak. Thus, a resulting identification performed based on the earliest detected oligo-DNA-derived peak erroneously recognized as the peak of the internal standard substance leads to an error in estimation of a size of an RNA or DNA.

In view of the above problem, it is an object of the present invention to provide a capillary electrophoresis method capable of electrophoresing an internal standard substance migrating faster than an analysis target substance, together with sample components, and identifying an earliest one of detected peaks as a peak derived from the internal standard substance, so as to accurately identify respective peaks of the sample components.

In order to achieve the above object, according to a first aspect of the present invention, there is provided a capillary electrophoresis method which comprises simultaneously introducing an unknown sample selected from the group consisting of proteins, nucleic acids and carbohydrates, and an internal standard substance to capillary electrophoresis, determining an earliest one of detected peaks as a peak derived from the internal standard substance, and identifying the remaining peaks on the basis of the internal standard substance-derived peak. In this method, the internal standard substance consists of a fluorescent substance or a salt thereof which has a positive or negative net charge of 2 or more in an electrolyte solution used for the capillary electrophoresis.

In the capillary electrophoresis method of the present invention, the internal standard substance may consist of a fluorescent substance having two or more acid groups or basic groups on a side chain thereof.

In the capillary electrophoresis method of the present invention, the fluorescent substance may consist of a fluorescein-based fluorescent substance.

In the capillary electrophoresis method of the present invention, the internal standard substance may be selected from the group consisting of 5(6)-carboxyfluorescein, 2',7'-bis(2-carboxyethyl)-5(and-6)-carboxyfluorescein, and 5-carboxy-(and-6)-fluorescein-sulfonic acid, trisodium salt.

In the capillary electrophoresis method of the present invention, the electrolyte solution used for the capillary electrophoresis may have a pH ranging from 5.0 to 10.0 at 25° C.

In the capillary electrophoresis method of the present invention, the unknown sample and the internal standard substance may be detected by fluorescence detection.

According to a second aspect of the present invention, there is provided a reagent kit for use in capillary electrophoresis, which comprises the internal standard substance set forth in the first aspect of the present invention.

As above, in the present invention, the internal standard substance migrating faster than components contained in the unknown sample as an analysis target is electrophoresed together with the unknown sample, and an earliest one of detected peaks is determined as a peak derived from the internal standard substance. Thus, the present invention can provide a capillary electrophoresis method capable of accurately identifying unknown peaks.

DETAILED DESCRIPTION OF THE PREFERRED EMBODIMENTS OF THE INVENTION

Figure 1:
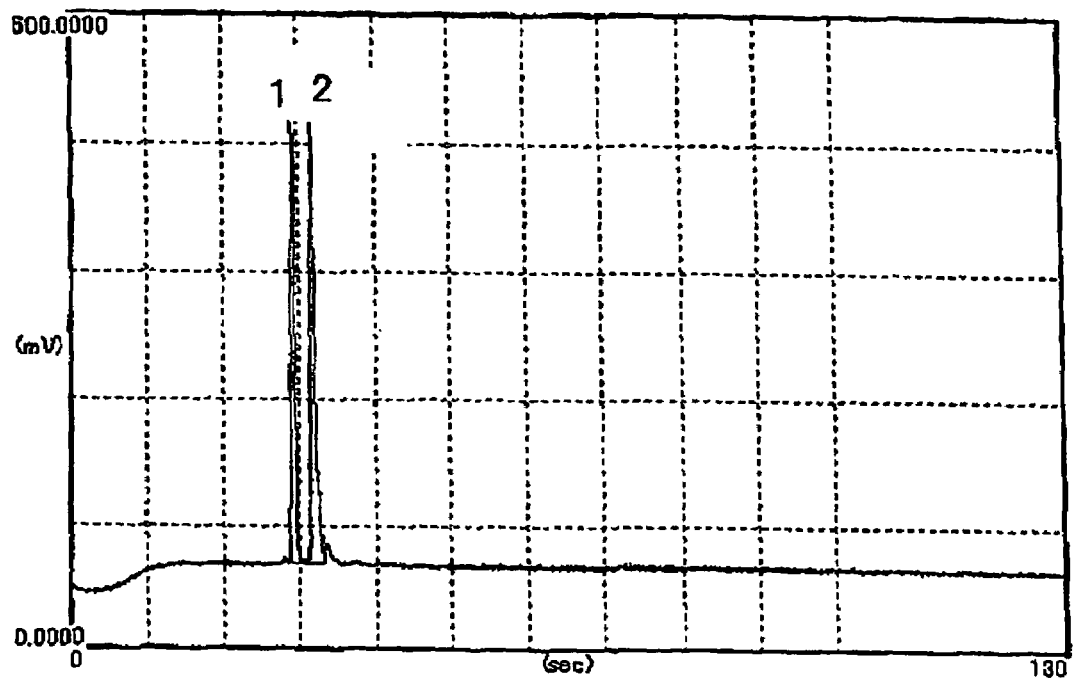
FIG. 1 is a graph showing an electropherogram for a mixture of a sample 1 and CF in Example 1.

In the present invention, a substance migrating faster than components contained in an unknown sample as an analysis target in a capillary electrophoresis process is used as an internal standard substance. The internal standard substance for use in the present invention is not limited to a specific substance as long as it is a fluorescent substance having a positive or negative net charge of 2 or more in an electrolyte solution used for the capillary electrophoresis.

The electrolyte solution for use in the capillary electrophoresis method of the present invention may be appropriately determined by those skilled in the art, depending on types of unknown samples as an analysis target and/or types of electrophoretic separation techniques, as will be described later. The unknown sample in the present invention is selected from the group consisting of proteins, nucleic acids and carbohydrates. The protein in the present invention means a protein which consists of about 100 to 2000 amino acids linked together and has an average molecular weight of 10,000 to 200,000. The nucleic acid in the present invention includes a nucleotide or nucleoside as a component of a nucleic acid, a double-stranded DNA or RNA, and a single-stranded DNA or RNA. The carbohydrate in the present invention comprises: a saccharide including a monosaccharide, such as galactose, fructose or mannose, a disaccharide, such as sucrose, lactose, maltose, cellobiose or trehalose, and a polysaccharide, such as dextran, cellulose, chitin and chitosan; a glycoprotein composed of a protein and a sugar chain linked thereto; and a sugar chain liberated from a glycoprotein.

The electrophoretic separation technique in the present invention may be appropriately selected by those skilled in the art, depending on the types of unknown samples. Specifically, the electrophoretic separation technique includes capillary zone electrophoresis (hereinafter referred to as "CZE") and capillary gel electrophoresis (hereinafter referred to as "CGE").

Typically, in the CZE, a capillary is filled with one type of electrolyte solution, and component ions contained in an unknown sample are separated based on an electroosmotic flow generated by electric double layers formed between an inner wall of the capillary and the electrolyte solution, and a difference between respective electrostatic forces of the component ions depending on electric charges and molecular weights thereof. In a material of a commonly used capillary, the electroosmotic flow toward a negative electrode is stronger than the electrostatic forces. Thus, it is desirable to use an internal standard substance which has a positive net charge of 2 or more, preferably 2 to 10, more preferably 2 to 8.

Further, in order to reduce the influence of the electroosmotic flow, the inner wall of the capillary may be subjected to a chemical or physical treatment. Specifically, polyacrylamide, polyethylene glycol, polyethylene imine, fluorine-containing aromatic hydrocarbon or saccharide may be fixed onto the inner wall of the capillary. If the inner wall of the capillary is modified to eliminate the electroosmotic flow, it is considered that an anionic component, for example, simply migrates toward a positive electrode, and its velocity is proportional to a charge/molecular weight ratio. In the case of separating an unknown sample containing components primarily having a negative charge in an electrolyte solution used, it is desirable to use an internal standard substance which has a negative net charge of 2 or more, preferably 2 to 10, more preferably 2 to 8. This allows the internal standard substance to migrate at a higher velocity than that of each components of the unknown sample exhibiting a negative charge. Conversely, in the case of separating an unknown sample containing components primarily having a positive charge, it is desirable to use an internal standard substance having a positive charge polarity.

In the CGE, a capillary is filled with a gel, such as polyacrylamide gel or agarose gel, and an electrolyte solution, and component ions contained in an unknown sample are separated based on a molecular sieving effect of the gel. The CGE further includes a capillary electrophoresis technique in which a capillary is filled with an electrolytic solution containing a hydrophilic polymer, such as non-cross-linked polyacrylamide, dextran or cellulose derivative, dissolved therein instead of a gel, and component ions contained in an unknown sample are separated based on a molecular sieving effect in the same manner as the above CGE. In this CGE using the electrolytic solution containing a hydrophilic polymer dissolved therein, an inner wall of the capillary is typically subjected to chemical modification. As one example of the chemical modification, a technique of chemically modifying using non-cross-linked polyacrylamide may be used when the capillary is made of silica, as disclosed in S. Hjorten, J. Chromatogr., 347, 191 (1985).

In the CGE, a buffer solution having a pH at 25° C. of 5.0 to 10.0, preferably 6.5 to 9.0, is used as the electrolyte solution. When the unknown sample is a protein or glycoprotein, a SDS (sodium dodecyl sulfate) gel electrophoresis technique may be used which is designed such that the unknown sample is denatured with a SDS micelle to equalize electric properties of protein molecules, and then introduced to size separation in a gel. In the SDS gel electrophoresis, the protein or glycoprotein will have an even negative charge per unit mass. Similarly, when the unknown sample is a nucleic acid, the nucleic acid will have a negative charge in an electrolyte solution used for the CGE. Thus, it is desirable to use an internal standard substance having a negative charge polarity. When the unknown sample is a saccharide or sugar chain, it is preferable to derivatize the saccharide or sugar chain using various types of fluorescent substances having an ionic functional group, and select an internal standard substance which has the same polarity as that of the derivatized saccharide or sugar chain at a selected pH of an electrolyte solution having a charge, as will be described later.

As one feature of the present invention, the internal standard substance consists of a fluorescent substance having a positive or negative net charge of 2 or more, preferably 2 to 10, more preferably 2 to 8, in an electrolyte solution appropriately selected by those skilled in the art, depending on the types of unknown samples and/or the types of electrophoretic separation techniques.

For example, a skeletal component of the fluorescent substance to be used in the present invention may include coumarin series, pyrene series, naphthalene series, fluorescein series, fluoranthene series, porphyrin series, quinoline series, and stilbenzene compounds, and a salt thereof. A light intensity of fluorescence is proportional to a concentration of the fluorescent substance irrespective of a composition of an electrolyte solution. Thus, the skeletal component of the fluorescent substance is preferably capable of generating fluorescence by itself without forming a complex in cooperation with metal.

Preferably, the skeletal component of the fluorescent substance may include fluorescein series. The salt of the fluorescent substance is not limited to a specific one, but may include a Na salt, an Mg salt and a K salt. When the skeletal component has no charge, a derivative having an ionic functional group such as an acid group or a basic group may be prepared using a conventional technique. Those skilled in the art can prepare a derivative from a compound with the above skeletal component, using a conventional technique.

The acid group may include a hydroxyl group (—OH), a carboxyl group (—COOH), a sulfonic acid group (—SO$_3$H), a phosphate group (—OPO$_3$H), a sulfate group (—OSO$_3$H) and a phosphono group (—PO$_3$H$_2$). The basic group may include an amino group (—NH$_3$) and an imino group (=NH).

The internal standard substance in the present invention is prepared such that a side chain thereof includes at least two or more of the above acid groups or basic groups, and the type and number of the functional groups are determined in consideration of respective acid dissociation constants of the functional groups to allow the internal standard substance to have a desirable net charge in an electrolyte solution used.

The salt of the fluorescent substance may be preferably used to facilitate dissociation in the ionic functional group.

As above, the fluorescent substance is used as a skeletal component of the internal standard substance in the present invention. Thus, in a capillary electrophoresis method for detecting an unknown sample and an internal standard substance based on a fluorescence detection technique, the detection can be performed without further fluorescent-labeling to the internal standard substance.

Specifically, the internal standard substance in the present invention may include: 5(6)-carboxyfluorescein (hereinafter referred to as "CF"); 2',7'-bis (2-carboxyethyl)-5(and-6)-carboxyfluorescein (hereinafter referred to as "BCECF"); 5-carboxy-(and-6)-fluorescein-sulfonic acid, trisodium salt (hereinafter referred to as "CFS-3Na"); and bis [N,N-bis (carboxymechyl) aminomethyl] fluoresceine.

Each of the CF, BCECF and CFS-3Na can be suitably used in a capillary electrophoresis method using an electrolysis solution having a pH of 5.0 to 10.0 (25° C.).

Each of these fluorescent substances is desirably capable of generating fluorescence by itself. Further, each of the CF and BCECF allows an internal standard substance-derived peak to be desirably represented as a single peak.

The present invention also provides a reagent kit for use in capillary electrophoresis. The reagent kit comprises at least the above internal standard substance, and may additionally include a buffer solution and a polymer solution. The buffer solution may be appropriately selected depending on the types of unknown samples and electrophoretic modes, as described above. For example, a reagent kit for use in the CGE may include a buffer solution which contains 0.05 to 10 (w/v) % of non-cross-linked polyacrylamide or hydroxycellulose and has a pH of 5.0 to 10.0 (25° C.).

A capillary electrophoresis apparatus for use in the present invention may be a capillary electrophoresis apparatus using a capillary as a separating channel, or a capillary electrophoresis apparatus using a device (so-called microchip) comprising a base plate which has a micro-channel formed therein using microelectromechanical-system techniques to serve as a separating channel. The capillary or the base plate of the capillary electrophoresis apparatus may be made of a material which includes glass, fused silica and fluorine-containing hydrocarbon resin. The separating channel (in this specification, it is also referred to as "capillary") has an inner diameter of 10 to 1000 μm, preferably 50 to 200 μm. Preferably, the capillary has an inner wall modified depending on the types of unknown samples and electrophoretic separation techniques, as described above.

In the capillary electrophoresis apparatus using a capillary as a separating channel, an unknown sample may be introduced into the capillary through a process which includes a suction (vacuum) process, a pressure process, a gravity process and an electrokenetic process. In these processes, a sample is introduced into the capillary while immersing one end of the capillary in a solution of the sample. The internal standard substance in the present invention may be added to the sample solution, and introduced into the capillary in the form of a mixture with the sample. Alternatively, after the sample is introduced into the capillary, the internal standard substance may be dissolved in the same solvent as that of the sample solution, and introduced into the capillary in the form of a solution. In the capillary electrophoresis apparatus using a microchip, a sample may be introduced into the separating channel through the electrokenetic process, or a process of filling a sample solution in a sample-introducing channel additionally formed to intersect with the separating channel, and then introducing the sample solution filled in an intersecting portion of the separating channel, into the separating channel (so-called "cross injection process"). In the capillary electrophoresis apparatus using a microchip, the internal standard substance may be introduced into the separating channel after being mixed with the sample solution, or the sample solution and the internal-standard-substance solution may be sequentially introduced into the separating channel.

Preferably, the internal standard substance is introduced into the capillary in an amount substantially equal to that of a sample to be introduced into the capillary. An amount of the sample to be introduced into the capillary may be appropriately determined by those skilled in the art, in consideration of an inner diameter and/or channel length of the capillary and a fluorescence intensity to be detected.

In the capillary electrophoresis apparatus, the unknown sample and the internal standard substance are introduced to on-capillary detection in which they are detected by detection means disposed adjacent to an outlet of the capillary, while applying an electrophoretic voltage to maintain electrophoretic migration. In the present invention, the term "migration time" means a "time period from a time when the electrophoretic voltage is applied after the unknown sample is introduced into the capillary, through until a component of the unknown sample or the internal standard substance reaches the detection means". A fluorescence detector may be used as the detection means. A xenon lamp, a halogen lamp, a deuterium discharge tube or a laser may be used as a light source for exciting light. The laser is desirable to allow the detection to be performed with high sensitivity. Specifically, the laser may include an argon laser (wavelength: 457 nm, 488 nm, 514.5 nm), a helium-cadmium laser (wavelength: 442 nm) and a helium-neon laser (wavelength: 543.5 nm). It is necessary to select a light source capable of emitting a light having an excitation wavelength for the unknown sample (including an after-mentioned fluorescent-labeled unknown sample) and the internal standard substance for use in the present invention. For example, when either one of the CF, BCECF and CFS-3Na is used as the internal standard substance, a laser having an excitation wavelength of 450 to 500 nm is selected.

If components of the unknown sample generate no fluorescence or only very weak fluorescence, by themselves, it is preferable to modify the sample with a fluorescent substance. Specifically, when the unknown sample is a DNA or RNA, a fluorescent dye, such as ethidium bromide, capable of being intercalated between a base pair of the DNA or RNA, is contained in an electrolyte solution. Then, by taking advantage of a property of the fluorescent dye that fluorescence to be generated therefrom the fluorescent dye is amplified by the intercalation, the detection means is operable to emit exciting light to the fluorescent substance intercalated in the DNA or RNA during electrophoresis, and detect fluorescence generated from the fluorescent substance.

Even if the unknown sample is a protein or sugar chain, the protein or sugar chain can be modified with a fluorescent substance by a conventional technique. Specifically, as for a protein or glycoprotein, a technique of inducing a reaction between phenylisothiocyanate and a ε-amine group on a side chain of lysine as one of amino acids constituting the protein or glycoprotein, may be used. As for saccharide or sugar chain, there are a pyridylamination process of modifying the saccharide or sugar chain with 2-aminopyridine (hereinafter referred to as "AP"), and a derivatization process of derivatizing the saccharide or sugar chain with 8-aminonaphthalene-1,3,6-trisulfonic acid (hereinafter referred to as "ANTS"). The saccharide or sugar chain derivatized with the AP will have a positive charge in an acidic region due to an imino group introduced therein The saccharide or sugar chain derivatized with the ANTS will have a negative charge due to a sulfonic acid group, or a strong acid group, introduced therein.

A process of identifying each peak detected through the capillary electrophoresis method of the present invention includes estimating a molecular weight or calculating a peak concentration from a peak area. In particular, when the unknown sample is a nucleic acid, the identification process includes estimating a size thereof.

Generally, a migration time of an analysis target substance in electrophoresis slightly varies in every analysis. Thus, a molecular weight or size estimated based on only an actual measurement value of a migration time is highly likely to cause difficulty in obtaining an estimate value with a high degree of accuracy. Therefore, it is desirable to provide a mechanism for correcting a variation in each analysis. For this purpose, in general, the unknown sample and the internal standard substance are electrophoresed together, and, on the basis of an internal standard substance-derived peak, remaining detected peaks are identified.

In the present invention, the aforementioned fluorescence substance used as the internal standard substance makes it possible to readily recognize an earliest one of detected peaks as a peak derived from the internal standard substance. This is useful in a data analysis program. It is understood that the earliest peak is determined excluding a noise peak in the detected peaks. The peaks include peaks on an electropherogram representing an analysis result, and bands in a gel image representing an analysis result While a more specific identification process will be described below, the present invention is not limited to the specific process. When the electrophoretic separation technique is the CGE, sample components are separated according to a difference in molecular weight. Thus, a relationship between a molecular weight and a migration time can be obtained based on a molecular weight of the internal standard substance. A molecular weight of a sample component corresponding to an unknown peak can be estimated from this relationship.

For example, when the unknown sample is a nucleic acid, and it is intended to estimate a size thereof, the following process may be performed. A solution containing two types or more of nucleic acids each having a known size (this solution will hereinafter be referred to as "size marker solution") can be analyzed to express a relationship between a size and a migration time, as a function. Further, the unknown sample or the size marker solution is electrophoresed simultaneously together with the aforementioned internal standard substance in the present invention, and a migration time in each analysis is corrected. Then, a size of each sample component corresponding to detected peaks other than the earliest peak is estimated as well as other identifications, using a separately-calculated function of a size and a migration time.

A HMW-side internal standard substance may be additionally electrophoresed together with the internal standard substance in the present invention, and a last one of the detected peaks may also be used as a reference peak. The HMW-side internal standard substance means a substance which falls within a molecular weight range capable of being separated with a certain resolution and has a molecular weight greater than those of substances contained in the unknown sample. When the unknown sample is a nucleic acid, a nucleic acid having a known size may be used as the HMW-side internal standard substance, as disclosed in the Non-Patent Publication 1.

While the present invention will be more specifically described by taking some examples thereof the present invention is not limited to the following Examples.

In the Examples, the following two samples having a minimum size as a sample for analyzing a size of a RNA or DNA in capillary electrophoresis using a polymer solution were prepared:

Sample 1: 7-mer oligo-DNA without fluorescent labeling

Sample 2: deoxynucleotide-5'-triphosphate modified with fluorescein

Generally, a commercially-available single-stranded oligo-DNA having a minimum size is a 7-mer oligo-DNA. Thus, when a DNA or RNA is selected as an analysis target, the sample 1 can be considered as an oligo-DNA having a minimum size. While a 1-mer DNA is also commercially available, the DNA generate no fluorescence by itself, and a fluorescent substance mixed in an electrophoretic buffer is not intercalated in the DNA. Thus, the sample 2 was prepared as a 1-mer DNA.

EXAMPLE 1

Carboxyfluorescein (CF) is Used as the Internal Standard Substance 5.7 μg of the sample 1 was dissolved in 100 μL of 10 mM Tris-1 mM EDTA (TE buffer, pH 8.0) to prepare a sample solution 1. In the same manner, 6.0 ng of the sample 2 was dissolved in 1000 μL of 10 mM Tris-1 mM EDTA (TE buffer, pH 8.0) to prepare a sample solution 2. 20 ng of CF as the internal standard substance was added to each of the sample solution 1 and the sample solution 2. Then, each of the obtained sample solutions 1, 2 was set in a laser-excitation fluorescence-detection type (solid-state laser, wavelength: 473 nm) capillary electrophoresis apparatus (MCE-2010, produced by Shimadzu Co.). 2.0 (w/v) % of hydroxyethyl-cellulose (average molecular weight: 250,000, produced by Aldrich Chemical Co.) was dissolved in 180 mM Tris-180 mM boric acid-0.05M EDTA (TBE buffer, pH 8.3) to prepare an electrolyte solution. The electrolyte solution contains 0.03 (w/v) % of SYBR Gold (produced by Invitrogen Corp.) as an intercalator dye. The sample 1 or the sample 2 was introduced into a separating channel together with the internal standard substance, through a cross injection process, and capillary electrophoresis was performed to obtain an electropherogram.

Figure 2:
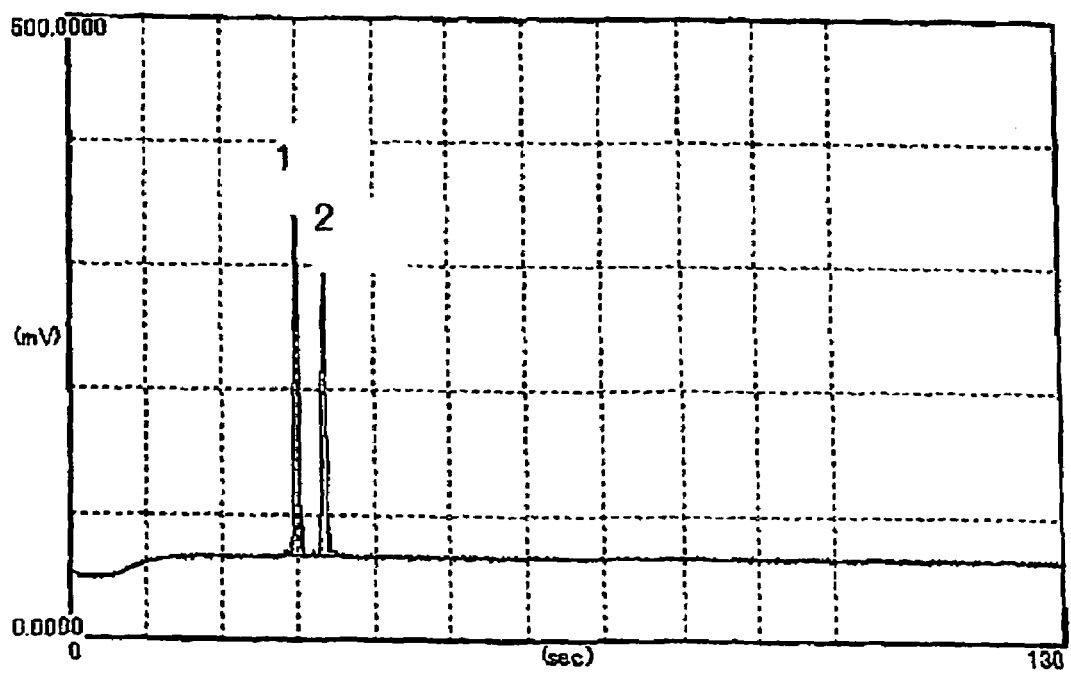
FIG. 2 is a graph showing an electropherogram for a mixture of a sample 2 and CF in Example 1.

FIG. 1 shows an electropherogram for a mixture of the sample 1 and the CF, and FIG. 2 shows an electropherogram for a mixture of the sample 2 and the CF. In FIG. 1, the peak 1 is a CF-derived peak, and the peak 2 is a sample 1-derived peak. In FIG. 2, the peak 1 is a CF-derived peak and the peak 2 is a sample 2-derived peak. These results verify that the CF is eluted earlier than the samples 1, 2.

EXAMPLE 2

BCECF is Used as the Internal Standard Substance

The sample solution 1 and the sample solution 2 were prepared in the same manner as that in Example 1. 20 ng of BCECF was added to 1 mL of each of the sample solution 1 and the sample solution 2, and capillary electrophoresis was performed under the same conditions as those in Example 1.

Figure 3:
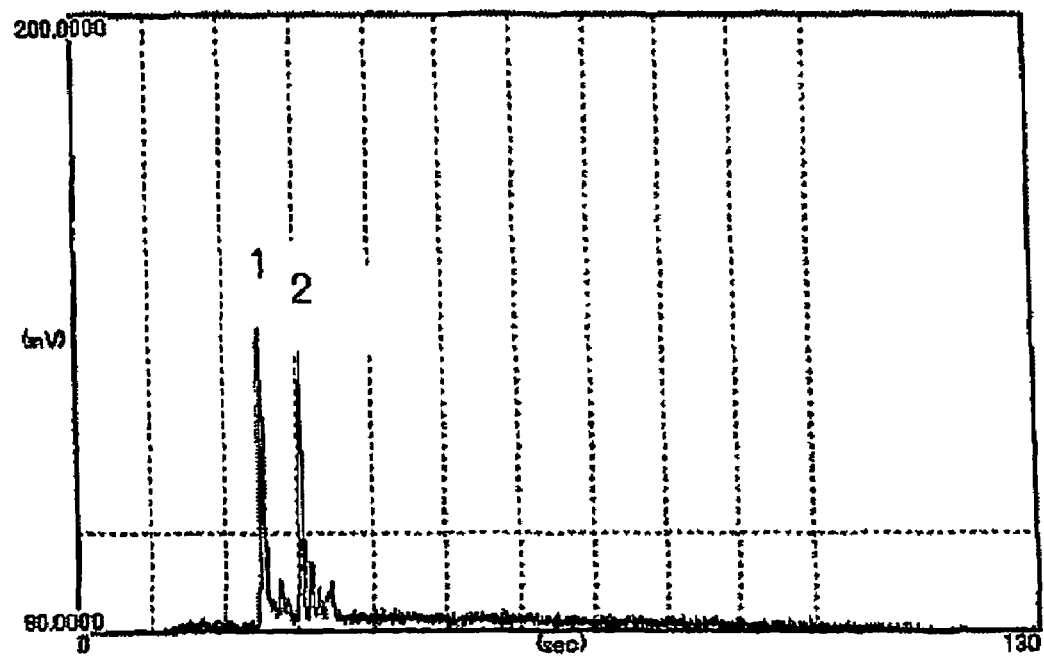
FIG. 3 is a graph showing an electropherogram for a mixture of a sample 1 and BCECF in Example 2.
Figure 4:
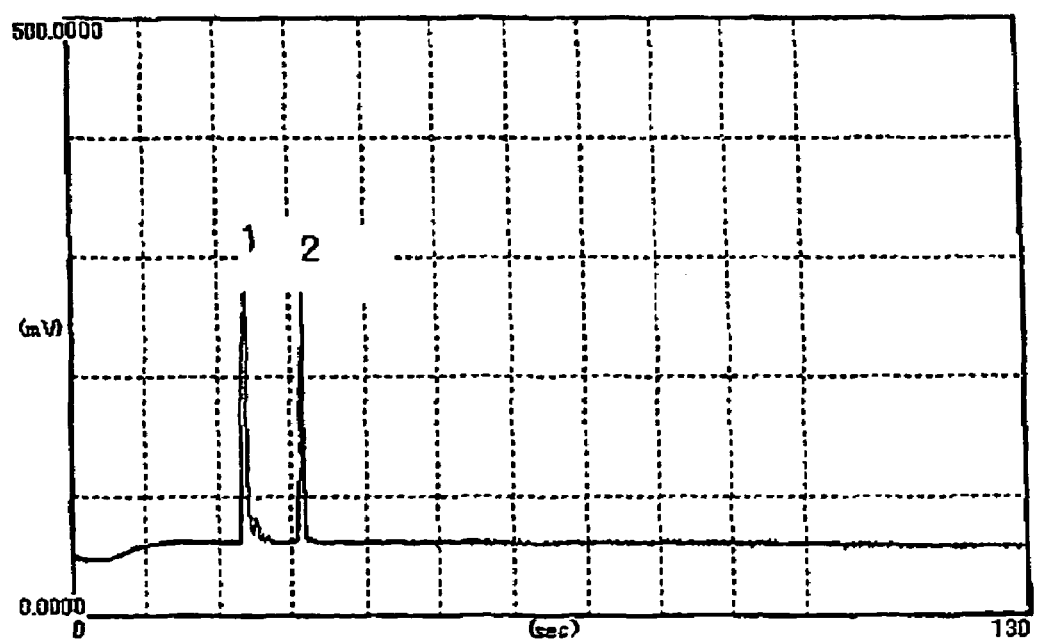
FIG. 4 is a graph showing an electropherogram for a mixture of a sample 2 and BCECF in Example 2.

FIG. 3 shows an electropherogram for a mixture of the sample 1 and the BCECF, and FIG. 4 shows an electropherogram for a mixture of the sample 2 and the BCECF. In FIG. 3, the peak 1 is a BCECF-derived peak, and the peak 2 is a sample 1-derived peak. In FIG. 4, the peak 1 is a BCECF-derived peak, and the peak 2 is a sample 2-derived peak.

These results verify that the BCECF is eluted earlier than the samples 1, 2.

In the same manner, it was verified that CFS-3Na is eluted earlier than the samples 1, 2.

As above, the internal standard substance in the present invention can generate an earliest one of detected peaks to allow the remaining peaks to be identified on the basis of the internal standard substance-derived peak.

Each of the CF, BCECF and CFS-3Na used in the examples can have a negative net charge of 2 or more in neutral to alkaline ranges, and has a relatively small molecular weight. Thus, these internal standard substances can be suitably used in capillary gel electrophoresis for separating molecules of a protein or a carbohydrate as well as a nucleic acid, particularly, based on a molecular sieving effect.

What is claimed is:

1. A capillary electrophoresis method comprising:
    simultaneously introducing an unknown sample and an internal standard substance to capillary electrophoresis, wherein said unknown sample is selected from the group consisting of proteins, nucleic acids and carbohydrates;
    determining an earliest one of detected peaks as a peak derived from said internal standard substance; and
    identifying the remaining peaks on the basis of said internal standard substance-derived peak,
    wherein said internal standard substance consists of a fluorescent substance or a salt thereof which has a positive or negative net charge of 2 or more in an electrolyte solution used for the capillary electrophoresis, and
    wherein said internal standard substance is selected from the group consisting of: 5(6)-carboxyfluorescein; 2',7'-bis(2-carboxyethyl)-5(and-6)-carboxyfluorescein; and 5-carboxy-(and-6)-fluorescein-sulfonic acid, trisodium salt, and bis[N,N-bis(carboxymethyl)aminomethyl]fluoresceine.

2. The capillary electrophoresis method as defined in claim 1, wherein said electrolyte solution used for the capillary electrophoresis has a pH ranging from 5.0 to 10.0 at 25° C.

3. The capillary electrophoresis method as defined in claim 1, wherein said unknown sample and said internal standard substance are detected by fluorescence detection.

4. A reagent kit for use in capillary electrophoresis, comprising the internal standard substance as defined in claim 1.

* * * * *